United States Patent
Walter et al.

(10) Patent No.: US 11,045,795 B2
(45) Date of Patent: Jun. 29, 2021

(54) CATALYTICALLY HIGHLY EFFECTIVE PRECIOUS METAL-CARBOXYLATE COMPOUNDS OF IR, RU, RH, PD AND AU

(71) Applicant: HERAEUS PRECIOUS METALS GMBH & CO. KG, Hanau (DE)

(72) Inventors: Richard Walter, Alzenau (DE); Horst Meyer, Altenstadt (DE); Steffen Voss, Los Alamitos, CA (US); Jan Schapp, Long Beach, CA (US)

(73) Assignee: HERAEUS PRECIOUS METALS GMBH & CO. KG, Hanau (DE)

( * ) Notice: Subject to any disclaimer, the term of this patent is extended or adjusted under 35 U.S.C. 154(b) by 311 days.

(21) Appl. No.: 15/879,681

(22) Filed: Jan. 25, 2018

(65) Prior Publication Data
US 2018/0147570 A1    May 31, 2018

Related U.S. Application Data

(60) Continuation of application No. 14/294,672, filed on Jun. 3, 2014, now abandoned, which is a division of application No. 12/531,795, filed as application No. PCT/EP2008/002186 on Mar. 19, 2008, now abandoned.

(30) Foreign Application Priority Data

Mar. 26, 2007   (DE) ..................... 10 2007 014 914.1

(51) Int. Cl.
| | | |
|---|---|---|
| *B01J 31/04* | (2006.01) | |
| *B01J 31/22* | (2006.01) | |
| *C07C 51/41* | (2006.01) | |
| *C07F 15/00* | (2006.01) | |

(52) U.S. Cl.
CPC .......... *B01J 31/04* (2013.01); *B01J 31/2239* (2013.01); *C07C 51/412* (2013.01); *C07F 15/0053* (2013.01); *B01J 2231/34* (2013.01); *B01J 2531/821* (2013.01); *B01J 2531/827* (2013.01)

(58) Field of Classification Search
None
See application file for complete search history.

(56) References Cited

U.S. PATENT DOCUMENTS

| 7,951,969 B2 | 5/2011 | Karch et al. |
| 2010/0234628 A1 | 9/2010 | Karch et al. |

FOREIGN PATENT DOCUMENTS

| CN | 1733599 | 2/2006 |
| CN | 1733599 B | * 2/2006 |
| DE | 1127888 | 4/1962 |
| DE | 100 35 841 A1 | 3/2001 |
| EP | 0 380 213 A2 | 8/1990 |
| EP | 0616997 | 9/1994 |
| EP | 0786447 | 7/1997 |
| EP | 0844251 | 5/1998 |
| EP | 1046629 | 2/2003 |
| GB | 2413323 A | 10/2005 |
| JP | 2 288842 A | 11/1990 |
| JP | 2008 542223 A | 11/2008 |
| WO | 96/23757 | 8/1996 |
| WO | 2006/125628 | 11/2006 |

OTHER PUBLICATIONS

English translation CN 1733599 B.*
Krogmann; Zeitschrift für anorganische und allgemeine Chemie; Band 358 May 1968, pp. 97-192.
Syamal, et al.; "Synthesis of new Platinum (II) complexes with ortho-Phenylenediamine ortho-Aminophenol, Ethanolamine and Oxygen-Donor Ligands"; Transition Met. Chem. 8, 280-282 (1983).
Hirota et al.; "The reducibility and polarography of Pd(II) complexes in aqueous solution"; J. Inorg. nucl. Chem. 1971, vol. 33, pp. 2617-2621.
Nakamura et al.: "Electron Spin Resonance of Pd(I). III The nature of the Metal-ligand Bonds in Square Planar Complexes of Palladium (I)"; J. Coord. Chem., 1971, vol. 1, pp. 221-228.
Nakamura et al.: "Electron Spin Resonance of Palladium (I). IV. Mixed-Ligand Complexes of Palladium(I)"; The Journal of Physical Chemistry, vol. 78, No. 21, 1974, pp. 2136-2140.
Pichugina et al.; "Gold Complexes with Oxygen-containing Ligands as a Catalyst for Methane Oxidation"; Gold Bulletin 2007, 40/2, pp. 115-119.
English Translation of: Allgemeines Fachwissen, Dkumentiert durch: Jander Blasius, Lehrbuch der analytischen und präparativen, 1965, pp. 194-201.
English Abstract of: K. Krogmann und P. Dodel, Chem. Ber. 1966 Jahrg. 99, pp. 3402-3418.
English Abstract of: K. Krogmann, Angew Chem., 1969, pp. 10-17.
English Abstract of: A.A. Grüberg, Helvetica Chimica Acta, 1931, 14, pp. 455-472.
Watson, "Precious Metals Catalysis Seminar", Oct. 1996, pp. 83-93.

* cited by examiner

*Primary Examiner* — Yun Qian
(74) *Attorney, Agent, or Firm* — Norris McLaughlin, P.A.

(57) ABSTRACT

Processes produce catalytically highly effective noble metal carboxylate compounds or their solutions that comprise A) a noble metal carboxylate, wherein the noble metal is selected from the group consisting of ruthenium, platinum, palladium, rhodium and gold, and B) at least one compound selected from the group consisting of oxalic acid, a salt of oxalic acid, a derivative of oxalic acid and a salt of the derivative of oxalic acid. The process digests the noble metal with alkaline earth peroxide to produce a digestion mass and dissolves the digestion mass in a carboxylic acid or a carboxylic acid diluted with a protic solvent to produce a resulting solution, whereby alkaline earth ions are separated off as salt of an oxalic acid or salt of oxalic acid derivatives, and the processes do not include any BaSO4 precipitation and filtration of barium sulphate.

6 Claims, No Drawings

CATALYTICALLY HIGHLY EFFECTIVE PRECIOUS METAL-CARBOXYLATE COMPOUNDS OF IR, RU, RH, PD AND AU

The present application is a continuation of U.S. patent application Ser. No. 14/294,672, filed Jun. 3, 2014, which is a divisional of U.S. patent application Ser. No. 12/531,795, filed Nov. 18, 2009, which is an application filed under 35 U.S.C. § 371 of PCT/EP2008/002186, filed Mar. 19, 2008, which claims foreign priority benefit under 35 U.S.C. § 119 of the German Patent Application No. 10 2007 014 914.1 filed Mar. 26, 2007.

The invention relates to catalytically highly effective noble metal carboxylate compounds of Ir, Ru, Rh, Pd, Pt and Au and to processes for their production.

A known use of iridium, ruthenium and their compounds is that as catalyst and catalyst precursor. Thus, according to EP 0 616 997 A1 and EP 0 786 447 A1, for example, iridium catalysts are used in carbonylation reactions. Iridium acetate, among others, is mentioned as iridium compound suitable for this purpose.

From the German patent application published for opposition (Auslegeschrift) 1 127 888 it is known to produce vinyl esters of higher carboxylic acids by reesterification of the vinyl esters of lower carboxylic acids in the presence of platinum group metal salts. Examples of suitable platinum group metal salts are, among others, the acetates of palladium and rhodium obtained from the hydroxides dissolved in glacial acetic acid by reaction with acetic anhydride.

EP 0 844 251 relates to the production of ruthenium carboxylate solutions from ruthenium(IV) oxide by reduction with hydrazine derivative in the presence of a carboxylic acid. The production of ruthenium oxide, in particular its filtration, is highly time consuming.

In EP 1 046 629, a process for the production of Ir acetate is described in which iridium hydroxide is precipitated from an aqueous solution of an chloroiridium compound with an aqueous solution of an alkali metal hydroxide, alkali metal carbonate or alkali metal hydrogen carbonate, the precipitated iridium hydroxide is separated off and reacted with acetic acid or a mixture of acetic acid/acetic anhydride to form a solution containing iridium acetate, and the iridium acetate is isolated from the solution as solid.

Watson describes the production of Ir acetate (Precious Metals Catalysts Seminar, page 83 ff.), in which Ir sponge is sintered with barium peroxide. Subsequently, the sintered mass is dissolved in a mixture of acetic acid/water and separated by filtration from non-reacted metal. Barium sulphate is then precipitated by the addition of sulphuric acid and separated from the iridium acetate solution by filtration. Subsequently, the iridium acetate solution is concentrated by evaporation. A key step of this process is careful balancing during the removal of the barium. Neither barium nor sulphates are desirable in the end-product. For this reason, a highly accurate adjustment is required in order to obtain the desired product.

This process has several disadvantages:

Accurately adjusting the sulphuric acid content is difficult to carry out and needs to be verified analytically. For this reason, repeated precipitation and filtration of barium sulphate together with the corresponding analytical investigations are necessary as a rule. A further disadvantage is the extremely difficult and cost-intensive filtration of the Ba sulphate. In addition, the concentration of the strontium contained therein cannot be sufficiently reduced by this precipitation route and consequently limits the purity of the product.

It is the object of the invention to provide catalytically highly effective noble metal carboxylate compounds of Ir, Ru, Rh, Pd, Pt and Au and a simple process for their production. The noble metal carboxylate compounds produced according to the process, in particular the acetate compounds, should be catalytically as highly effective as possible. Preferably, the compounds should also have a high purity and, in particular, have a low chlorine, sulphur, sodium and potassium content.

To achieve this object, a melt or fusion mass exhibiting noble metal and alkaline earth peroxide is dissolved in a carboxylic acid, if necessary with an addition of water, and subsequently filtered. From the filtered solution, the alkaline earth ions introduced by the alkaline earth peroxide are separated as salt of oxalic acid or salt of oxalic acid derivatives. Oxalate derivatives in the case of which an organic radical is arranged between the carboxyl groups have the same effect as oxalates. This process is highly efficient and circumvents time consuming $BaSO_4$ precipitation and the filtration of barium sulphate according to the Watson process. The purified noble metal carboxylate solution can be concentrated, it being possible to adjust the concentration increase to a desired concentration or to carry it out up to the isolation of the solid.

For this purpose, the methods corresponding to the state of the art such as evaporation of the reaction solution, spray drying or precipitation at a low temperature or addition of a suitable solvent are used. Surprisingly enough, the catalytic properties are particularly good when a noble metal carboxylate solution, in particular an acetic acid solution of ruthenium acetate or iridium acetate originates from the process using the precipitation of the alkaline earth metal as salt of oxalic acid or salt of oxalic acid derivatives. In a solution thus produced, the mass of oxalic acid and/or salts of oxalic acids or corresponding derivatives is smaller or equal to the mass of noble metal.

Preferably, the noble metals are digested with calcium peroxide or barium peroxide. Ruthenium and iridium are preferred noble metals. Acetate is the preferred carboxylate. The digested noble metal mixture dissolved in aqueous acetic acid is correspondingly preferred. According to the invention, the proportion of alkaline earth metal, in particular calcium, strontium or barium, amounts to 100 ppm to 10% by weight, in particular 500 ppm to 0.5% by weight, based on the noble metal, following precipitation as salt of oxalic acid or salt of oxalic acid derivatives. The calcium, strontium and barium content can be considerably reduced by fractional crystallisation.

EXAMPLE 1

1.5 g of ruthenium powder (14.8 mmole) and 10 g of barium peroxide (purity 95.8%; 56.5 mmole) are mixed.

The mixture is transferred into a nickel crucible and heated for 15 hours at 850° C.

150 ml of a mixture of acetic acid and water in a ratio of 2:1 are heated to 50° C. in a 200 ml three-necked flask.

The reaction mixture of ruthenium powder and barium peroxide is introduced into the three-necked flask. The mixture heats up to 80° C. by exothermic reaction. The mixture is heated to boiling temperature and stirred at boiling temperature for 3 hours.

Subsequently, the solution is cooled to room temperature and filtered through a membrane filter. The filter cake is washed with a little acetic acid/water mixture (2:1).

169 g of solution with an Ru content of 0.88% (1.487 g Ru, 14.7 mmole) and a Ba content of 4.59% (7.757 g Ba, 56.5 mmole) are obtained.

169 g of Ru acetate solution (1.487 g Ru, 14.7 mmole) are transferred into a 200 ml three-necked flask and 14.264 g of oxalic acid dihydrate (113 mmole) are added with stirring. After an agitation time of 4 hours the suspension is filtered on a black band filter and subsequently on a membrane filter. The filter cake is washed with acetic acid/water mixture (2:1).

230 g of solution with a Ru content of 0.57% (1.311 g Ru, 13 mmole) and a Ba content of 0.051% (0.117 g, 0.85 mmole) are obtained. The oxalate content (content determination by ion chromatography) is 0.36%.

EXAMPLE 2

1.5 g of ruthenium powder (14.8 mmole) and 10 g of barium peroxide (purity 95.8%; 56.5 mmole) are mixed.

The mixture is transferred into a nickel crucible and heated for 15 hours at 850° C.

150 ml of a mixture of acetic acid and water in a ratio of 2:1 are heated to 50° C. in a 200 ml three-necked flask.

The reaction mixture of ruthenium powder and barium peroxide is introduced into the three-necked flask. The mixture heats up to 76° C. by exothermic reaction. The mixture is heated to boiling temperature and stirred at boiling temperature for 3 hours. Subsequently, the solution is cooled to room temperature and filtered through a membrane filter. The filter cake is washed with a little acetic acid.

166 g of solution with an Ru content of 0.90% (1.494 g Ru, 14.8 mmole) and a Ba content of 4.67 (7.752 g Ba, 56.4 mmole) are obtained.

169 g of Ru acetate solution (1.494 g Ru, 14.8 mmole) are transferred into a 200 ml three-necked flask and 14.264 g of oxalic acid dihydrate (113 mmole) are added with stirring. After an agitation time of 4 hours the suspension is filtered on a black band filter and subsequently on a membrane filter. The filter cake is washed with acetic acid.

193 g of solution with a Ru content of 0.68% (1.314 g Ru, 13 mmole) and a Ba content of 0.0515% (0.1 g, 0.72 mmole) are obtained. The oxalate content (content determination by ion chromatography) is 0.26%.

EXAMPLE 3

5.001 g of rhodium powder and 34.622 g of barium peroxide were weighed into a glass with a screw cover and thoroughly mixed for 10 minutes. The mixture was transferred into a nickel crucible and subsequently heated at 850° C. for 15 hours in a muffle kiln. Subsequently, the crucible was cooled to room temperature. The melt is black at its surface, homogenous and grey underneath. The melt was introduced into a solution of acetic acid and fully demineralised water and stirred, while the ratio of acetic acid to water was 2:1 parts by volume. During this process, the temperature rose to 24° C. A dark green liquid with black particles was obtained. After further stirring for 15 minutes, the mixture was heated to 58° C. and kept at this temperature for 5 hours. During this process, the suspension adopted a brown colour within approximately 5 minutes. Subsequently, the barium was precipitated as salt with 51.453 grams of oxalic acid dehydrate and stirred for a further hour whereupon a yellow liquid was filtered off via a suction filter using a blue band filter. The filtrate was concentrated in a rotation evaporator at a temperature of 75° C. The rhodium acetate was dried up to mass constancy and ground using a mortar. The dried yield of rhodium acetate was 11.012 g. The rhodium content was determined by ICP analysis as being 34.43% by weight.

EXAMPLE 4

Iridium is digested with barium peroxide according to the Watson process and dissolved with acetic acid. The barium from the Watson process is precipitated with oxalic acid in a manner analogous to the above example 1 to 3 and filtered off. Such iridium carboxyl compounds, in particular acetates, exhibit unrivalled catalytic properties.

The invention claimed is:

1. A process for the production of catalytically highly effective noble metal acetate compounds or their solutions, wherein the catalytically highly effective noble metal acetate compounds or their solutions comprise A) a noble metal acetate, wherein the noble metal is selected from the group consisting of ruthenium, platinum, palladium, rhodium and gold, and B) at least one compound selected from the group consisting of oxalic acid, and a salt of oxalic acid, said process comprising:

mixing the noble metal with an alkaline earth peroxide to produce a mixture;

heating the mixture consisting of the noble metal and the alkaline earth peroxide to produce a melt exhibiting the noble metal and the alkaline earth peroxide;

dissolving the melt exhibiting the noble metal and the alkaline earth peroxide in an acetic acid or an acetic acid diluted with a protic solvent to produce a resulting solution;

introducing an oxalic acid into the resulting solution; and precipitating alkaline earth ions off the resulting solution as salt of an oxalic acid to produce a noble metal acetate compound or a noble metal acetate solution, wherein a proportion of alkaline earth metal in the noble metal acetate compound or the noble metal acetate solution amounts to 100 ppm to 10% by weight, based on the noble metal, following the precipitation as the alkaline earth salt of oxalic acid, wherein the process does not include any BaSO4 precipitation and filtration of barium sulphate.

2. The process according to claim 1, wherein the noble metal is ruthenium or iridium.

3. The process according to claim 1, wherein the alkaline earth ions are selected from the group consisting of Calcium, Barium and Strontium.

4. The process according to claim 1, wherein the protic solvent is water or an alcohol.

5. The process according to claim 1, wherein is the alkaline earth peroxide is calcium peroxide or barium peroxide.

6. The process according to claim 1, wherein the proportion of alkaline earth metal in the noble metal acetate compound or the noble metal acetate solution amounts to 500 ppm to 0.5% by weight, based on the noble metal, following the precipitation as alkaline earth salt of oxalic acid or salt.

* * * * *